United States Patent [19]

Tsutsumi et al.

[11] Patent Number: 5,081,112

[45] Date of Patent: Jan. 14, 1992

[54] METHOD FOR TREATING HYPERLIPIDEMIA

[75] Inventors: Kazuhiko Tsutsumi; Tagui Sugimoto, both of Tokushima; Yoshihiko Tsuda; Eiji Uesaka, both of Naruto; Kayoko Shinomiya, Tokushima; Yasuo Shoji, Tokushima; Atsushi Shima, Tokushima, all of Japan

[73] Assignee: Otsuka Pharmaceutical Factory Inc., Tokushima, Japan

[21] Appl. No.: 375,632

[22] Filed: Jul. 5, 1989

Related U.S. Application Data

[63] Continuation-in-part of Ser. No. 139,234, Dec. 29, 1987.

[30] Foreign Application Priority Data

Dec. 29, 1986 [JP] Japan ................................. 61-313267
Dec. 14, 1987 [JP] Japan ................................. 62-317246

[51] Int. Cl.$^5$ ............................................. A61K 31/66
[52] U.S. Cl. ................................. 514/119; 514/824
[58] Field of Search ............................. 514/119, 824

[56] References Cited

U.S. PATENT DOCUMENTS

| | | | |
|---|---|---|---|
| 3,073,740 | 1/1963 | Greenberg et al. | 514/119 |
| 4,232,010 | 11/1980 | Tsukamoto et al. | 424/200 |
| 4,268,507 | 5/1981 | Nguyen Mong | 424/217 |
| 4,309,364 | 1/1982 | Bentzen et al. | 260/931 |
| 4,371,527 | 2/1983 | Bentzen et al. | 424/204 |
| 4,416,877 | 11/1983 | Bentzen et al. | 424/204 |
| 4,607,031 | 8/1986 | Yoshino et al. | 514/211 |
| 4,822,780 | 4/1989 | Tsuda et al. | 514/119 |

FOREIGN PATENT DOCUMENTS

| | | |
|---|---|---|
| 0015370 | 9/1980 | European Pat. Off. |
| 0016310 | 10/1980 | European Pat. Off. |
| 0211346 | 2/1987 | European Pat. Off. |
| 0273444 | 7/1988 | European Pat. Off. |
| 61-151199 | 7/1986 | Japan |

OTHER PUBLICATIONS

Merck Manual, 14th edition, 1982, pp. 970–977.
Chem Abstracts 106:67489s, Tsuda et al. (1986).
Kluger et al., *J. Amer. Chem. Soc.*, 95:2362–2364 (1973).
Kluger et al., *J. Amer. Chem. Soc.*, 98:4913–4917 (1976).

*Primary Examiner*—Frederick E. Waddell
*Assistant Examiner*—Raymond J. Henley, III
*Attorney, Agent, or Firm*—Sughrue, Mion, Zinn, Macpeak & Seas

[57] ABSTRACT

A pharmaceutical composition for treating hyperlipidemia containing, as the active ingredient, at least one carboxamide compounds represented by the formula (1) which possess excellent activities in lowering serum lipid, as well as having low toxicity with high safety.

Said carboxamide compounds represented by the formula (1) are known compounds developed by the present inventors, but the pharmacological activities for treating hyperlipidemia have not been found yet.

12 Claims, No Drawings

METHOD FOR TREATING HYPERLIPIDEMIA

CROSS REFERENCE TO RELATED APPLICATION

This is a continuation-in-part of application Ser. No. 07/139,234, Dec. 29, 1987 pending.

FIELD OF THE INVENTION

The present invention relates to a pharmaceutical composition for treating hyperlipidemia. More particularly, the invention relates to a pharmaceutical composition for treating hyperlipidemia containing, as the active ingredient, a specific carboxamide compound.

PRIOR ART

Because of recent improvements of living conditions and westernization of eating habits in these days, as well as increasing of the aging population, there has been reported rapid increasing of number of the patients who are suffered from hyperlipidemia and from arteriosclerosis caused thereby.

Generally, hyperlipidemia is defined as pathogenic conditions due to abnormal increase of the serum lipids, thus due to abnormal increase of any one of chloresterol, triglycerides phospholipids or free fatty acids contained in the blood. Furthermore, hyperlipidemia is considered as an important risk factor of arteriosclerosis, especially of coronary arteriosclerosis, so that developments of methods for treating and preventing these diseases become social subject due to the increasing of number of the patients who are suffered from such diseases.

On the other hand, as to the methods for treating and curing hyperlipidemia, several therapies, such as dietetic therapy, therapeutic exercise and drug therapy and the like have been applied. For the above-mentioned drug therapy, a number of drugs have been studies and developed, and some of them are now commercially available. Among such commercially available drugs, for example, Clofibrate type drugs which are typical ones have been developed for the purpose of lowering the concentration of lipids, such as cholesterols, triglycerids, etc. in blood. These known drugs are classified in terms of their pharmacological mechanism as follows:

(1) Lipid absorption inhibiting agent,
(2) Lipid bio-synthesis inhibiting agent,
(3) Lipid dissimilation-excretion promoting agent,
(4) Lipoprotein metabolism improving agent, and
(5) Peroxidized lipid lowering agent.

PROBLEMS TO BE SOLVED BY THE INVENTION

The drugs for treating hyperlipidemia are specifically required their safety as higher as possible, since these drugs are to be administered for long period in view of the character of the disease.

However, drugs for treating hyperlipidemia known in the art and thus used widely, for example Clofibrate show certain drawbacks and side-effects, such as they induce efflorescence, muscle ache, tenderness, liver function disturbance, etc., thus in using these drugs considerable care should be paid. According to a report on the results of animal test conducted in a foreign country, the formation of hepatic tumor was observed in administration of the above-mentioned Clofibrate in a large amount for a long period of time. [Cf. YAKKYOKU (Pharmacy), Vol. 31, No. 11, page 31, (1980)].

Other drugs for treating hyperlipidemia, except the above-mentioned Clofibrate type drugs, the safety of these drugs are not sufficient, and thus some of them induce hepatopathy as side-effect and which will cause important problems in prolonged administration.

Furthermore, anyone of commercially available drugs for treating hyperlipidemia cannot show lipid lowering activity, and thus a drug having more excellent pharmacological activities are expected to be developed.

SUMMARY OF THE INVENTION

An object of the present invention is to provide novel drugs for treating hyperlipidemia, having excellent pharmacological activities, especially having the activity for lowering lipid in blood with high safety (less side effects) by eliminating the all of these drawbacks shown by conventional known drugs therefor.

Another object of the present invention is to provide a pharmaceutical composition for treating hyperlipidemia containing, as the active ingredient, a specific carboxamide compound.

Further object of the present invention is to provide a method for treating hyperlipidemia by administering a specific carboxamide compound.

DETAILED EXPLANATION OF THE INVENTION

In view of the above-mentioned circumstances in the known drugs for treating hyperlipidemia, the present inventors have made extensive studies to develop the drugs, and found the facts that specific carboxamide compound represented by the formula (1) as shown below possess pharmacological activities suitable for drugs for treating hyperlipidemia, especially possess excellent activities in lowering lipid in blood, as well as having low toxicity with high safety. Thus the present invention was successfully established.

The present invention relates to a pharmaceutical composition for treating hyperlipidemia containing, as the active ingredient, a carboxamide compound represented by the formula (1),

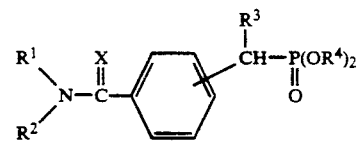

wherein $R^1$ and $R^2$ are each a hydrogen atom, a $C_{1-15}$ alkyl group, a $C_{3-8}$ cycloalkyl group, a diphenyl-$C_{1-6}$ alkyl group or a group of the formula,

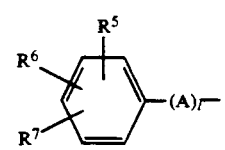

(wherein $R^5$, $R^6$ and $R^7$ are each a hydrogen atom, a halogen atom, a nitro group, a $C_{1-6}$ alkoxy group, a $C_{1-6}$ alkoxycarbonyl group, a $C_{1-6}$ alkyl group, a halogen-substituted $C_{1-6}$ alkyl group, a cyano group, a carboxyl group or a hydroxyl group; A is a $C_{1-4}$ alkylene group; l is 0 or 1); further, $R^1$ and $R^2$ together with the nitrogen atom being bonded thereto may form a heterocyclic group, with or without additional nitrogen atom or oxygen atom, and said heterocyclic group is unsubstituted or substituted with a $C_{1-6}$ alkyl group, a phenyl-$C_{1-6}$ alkyl group, a phenyl group, or substituted phenyl group having substituents selected from the group consisting of a $C_{1-6}$ alkyl group, a $C_{1-6}$ alkoxy group, a halogen atom and a halogen-substituted $C_{1-6}$ alkyl group; $R^3$ is a hydrogen atom, a $C_{1-15}$ alkyl group or a phenyl-$C_{1-6}$ alkyl group; $R^4$ is a $C_{1-6}$ alkyl group or a phenyl group; and X is an oxygen or sulfur atom.

Specifically, the pharmaceutical composition for treating hyperlipidemia contains, as the active ingredient, a carboxamide compound represented by the formula (1), wherein $R^1$ and $R^2$ are each a hydrogen atom, a $C_{1-6}$ alkyl group, a $C_{3-8}$ cycloalkyl group or a group of the formula,

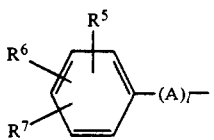

(wherein $R^5$, $R^6$ and $R^7$ are each a hydrogen atom, a halogen atom, a $C_{1-6}$ alkyl group, a $C_{1-6}$ alkoxy group, a halogen-substituted $C_{1-6}$ alkyl group, a cyano group or a nitro group; A is a $C_{1-4}$ alkylene group; l is 0 or 1); $R^3$ is a hydrogen atom; and $R^4$ is a $C_{1-6}$ alkyl group.

Furthermore, the pharmaceutical composition for treating hyperlipidemia contains, as the active ingredient, a carboxamide compound represented by the formula (1), wherein $R^1$ and $R^2$ are each a hydrogen atom, a $C_{1-6}$ alkyl group, or a group of the formula,

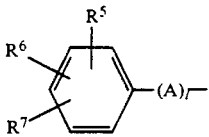

(wherein $R^5$, $R^6$ and $R^7$ are each a hydrogen atom, a halogen atom, a $C_{1-6}$ alkyl group, a halogen-substituted $C_{1-6}$ alkyl group or a cyano group; A is a $C_{1-4}$ alkylene group; l is 0 or 1); $R^3$ is a hydrogen atom; and $R^4$ is a $C_{1-6}$ alkyl group.

The pharmaceutical composition for treating hyperlipidemia according to the present invention specifically contains, as the active ingredient, at least one carboxamide compound selected from the group consisting of:
4-diethoxyphosphinoylmethyl-N-phenylbenzamide,
4-diethoxyphosphinoylmethyl-N-(4-chlorophenyl)benzamide,
4-diethoxyphosphinoylmethyl-N-(4-bromophenyl)benzamide,
4-diethoxyphosphinoylmethyl-N-(4-iodophenyl)benzamide,
4-diethoxyphosphinoylmethyl-N-(4-fluorophenyl)benzamide,
4-diethoxyphosphinoylmethyl-N-(4-trifluoromethylphenyl)benzamide,
4-diethoxyphosphinoylmethyl-N-(4-cyanophenyl)benzamide,
4-diethoxyphosphinoylmethyl-N-(3,4-dichlorophenyl)benzamide,
4-diethoxyphosphinoylmethyl-N-(4-chloro-3-trifluoromethylphenyl)benzamide,
4-diethoxyphosphinoylmethyl-N-benzyl-N-(4-chlorophenyl)benzamide,
4-diethoxyphosphinoylmethyl-N-(4-chlorobenzyl)-N-(4-chlorophenyl)benzamide,
4-diethoxyphosphinoylmethyl-N-benzyl-N-(4-trifluorophenyl)benzamide,
4-diethoxyphosphinoylmethyl-N-benzyl-N-(3,4-dichlorophenyl)benzamide,
4-diethoxyphosphinoylmethyl-N-(4-chlorobenzyl)-N(3,4-dichlorophenyl)benzamide,
4-diethoxyphosphinoylmethyl-N-benzyl-N-(4-chloro-3-methylphenyl)benzamide,
4-diethoxyphosphinoylmethyl-N-methyl-N-phenylbenzamide,
4-diethoxyphosphinoylmethyl-N-(4-chlorophenyl)-N-methylbenzamide,
4-diethoxyphosphinoylmethyl-N-(4-methylphenyl)benzamide,
4-diethoxyphosphinoylmethyl-N-(4-methoxyphenyl)benzamide,
4-diethoxyphosphinoylmethyl-N-(4-nitrophenyl)benzamide, 4-diisopropoxyphosphinoylmethyl-N-(2-phenylethyl)benzamide,
4-diethoxyphosphinoylmethyl-N-(4-chlorophenyl)-N-cyclopentylbenzamide,
4-diethoxyphosphinoylmethyl-N-benzyl-N-(4-nitrophenyl)benzamide,
4-diethoxyphosphinoylmethyl-N-(4-bromo-2-cyanophenyl)benzamide,
4-diethoxyphosphinoylmethyl-N-(4-chloro-2-cyanophenyl)benzamide,
4-diethoxyphosphinoylmethyl-N-(4-cyano-2-chlorophenyl)benzamide,
4-diethoxyphosphinoylmethyl-N-(4-iodo-2-cyanophenyl)benzamide,
4-diethoxyphosphinoylmethyl-N-(4-cyano-2-bromophenyl)benzamide,
4-diethoxyphosphinoylmethyl-N-(4-bromo-3-cyanophenyl)benzamide, and
4-diethoxyphosphinoylmethyl-N-(4-cyano-2-iodophenyl)benzamide.

In the above-mentioned formula (1), the substituents represented by the symbols of $R^1$ to $R^7$, A and X are exemplified as follows.

As to the $C_{1-15}$ alkyl group, methyl, ethyl, propyl, isopropyl, butyl, t-butyl, pentyl, hexyl, heptyl, octyl, nonyl, decyl, undecyl, dodecyl, tridecyl, tetradecyl and pentadecyl groups and the like can be exemplified.

As to the $C_{3-8}$ cycloalkyl group, cyclopropyl, cyclobutyl, cyclopentyl, cyclohexyl, cycloheptyl and cyclooctyl groups and the like can be exemplified.

As to the halogen atom, fluorine atom, chlorine atom, bromine atom and iodine atom can be exemplified.

As to the $C_{1-6}$ alkoxy group, methoxy, ethoxy, propoxy, isopropoxy, butoxy, t-butoxy, pentyloxy and hexyloxy groups and the like can be exemplified.

As to the $C_{1-6}$ alkoxycarbonyl group, methoxycarbonyl, ethoxycarbonyl, propoxycarbonyl, isopropoxycarbonyl, butoxycarbonyl, t-butoxycarbonyl, pentyloxycarbonyl and hexyloxycarbonyl groups and the like can be exemplified.

As to the $C_{1-6}$ alkyl group, methyl, ethyl, propyl, isopropyl, butyl, t-butyl, pentyl and hexyl groups and the like can be exemplified.

As to the halogen-substituted $C_{1-6}$ alkyl group, trifluoromethyl, trichloromethyl, 2,2,2-trifluoroethyl, 4- bromobutyl, 5-chloropentyl, 6-fluorohexyl groups and the like can be exemplified.

As to the diphenyl-$C_{1-6}$ alkyl group, diphenylmethyl, 2,2,-diphenylethyl, 3,3-diphenylpropyl, 4,4-diphenylbutyl, 3,5-diphenylpentyl and 4,6-diphenylhexyl groups and the like can be exemplified.

As to the phenyl-$C_{1-6}$ alkyl group, benzyl, α-phenethyl, β-phenethyl, 3-phenylpropyl, 4-phenylbutyl, 2-methyl-2-phenylethyl, 2-methyl-3-phenylpropyl, 5-phenylpentyl and 6-phenylhexyl groups and the like can be exemplified.

As to the $C_{1-4}$ alkylene group, methylene, ethylene, methylmethylene, 1-methylethylene, trimethylene, 2-methylpropylene and tetramethylene groups can be exemplified.

As to the substituted phenyl group having substituents selected from the group consisting of a $C_{1-6}$ alkyl group, a $C_{1-6}$ alkoxy group, a halogen atom and a halogen-substituted $C_{1-6}$ alkyl group, in addition to a phenyl group, 4-methylphenyl, 3-trifluoromethylphenyl, 3,4-dimethylphenyl, 3,4,5-trimethylphenyl, 2-ethylphenyl, 4-trichloromethylphenyl, 2-methoxyphenyl, 3,4-dimethoxyphenyl, 3,4,5-trimethoxyphenyl, 3-ethoxyphenyl, 4-methoxyphenyl, 4-propylphenyl, 3-t-butylphenyl, 4-pentylphenyl, 4-hexylphenyl, 4-propoxyphenyl, 3-t-butoxyphenyl, 4-pentyloxyphenyl, 4-hexyloxyphenyl, 4-(2-bromoethyl)phenyl, 3-(3-chloropropyl)phenyl, 4-(4-fluorobutyl)phenyl, 4-(5-chloropentyl)phenyl, 4-(6-bromohexyl)phenyl, 4-chlorophenyl, 3,4-dichlorophenyl, 2,6-dichlorophenyl, 3,4,5-trichlorophenyl, 3,4-dibromophenyl, 4-fluorophenyl, 2-fluorophenyl, 2-chlorophenyl, 4-bromophenyl, 4-chloro-2-methylphenyl and 3,4-dimethoxy-2-chlorophenyl groups and the like can be exemplified.

As to the group of the formula,

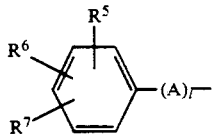

(wherein l=0), in addition to the above exemplified phenyl group and the substituted phenyl groups, a substituted phenyl group having substituents selected from the group consisting of a nitro group, a hydroxyl group, a cyano group, a carboxyl group and a halogen atom, the examples are included such as 4-nitrophenyl, 2-nitrophenyl, 2-methoxycarbonylphenyl, 2-hydroxy-4-ethoxycarbonylphenyl, 4-cyanophenyl, 2-cyanophenyl, 2-carboxyphenyl, 4-carboxyphenyl, 2-hydroxyphenyl, 4-hydroxyphenyl, 2-hydroxy-4-methylphenyl, 4-methoxycarbonylphenyl, 4-propoxycarbonylphenyl, 3-pentyloxycarbonylphenyl, 4-butoxycarbonylphenyl, 3-hexyloxycarbonylphenyl, 4-bromo-2-cyanophenyl, 4-chloro-2-cyanophenyl, 4-cyano-2-chlorophenyl, 4-iodo-2-cyanophenyl, 4-cyano-2-bromophenyl, 4-bromo-3-cyanophenyl and 4-cyano-2-iodophenyl groups and the like.

As to the group of the formula,

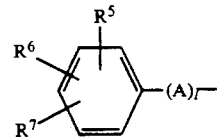

(wherein l=1), benzyl, α-phenethyl, β-phenethyl, 3-phenylpropyl, 4-phenylbutyl, 4-methylbenzyl, 2,5-dimethylbenzyl, 3-trifluoromethylbenzyl, 2-ethylbenzyl, 4-trichloromethylbenzyl, α-(2-methoxyphenyl)ethyl, β-(3,4-dimethoxyphenyl)ethyl, 3-ethoxybenzyl, 4-methoxybenzyl, 4-chlorobenzyl, 2,4-dichlorobenzyl, α-(2,6-dichlorophenyl)ethyl, 3,4-dibromobenzyl, α-(4-fluorophenyl)ethyl, 2-fluorobenzyl, 2-chlorobenzyl, 3,4-dimethoxy-2-chlorobenzyl, 2-nitrobenzyl, 3-(4-nitrophenyl)propyl, 4-nitrobenzyl, 4-(2-bromoethyl)benzyl, 3-(3-chloropropyl)benzyl, 4-(4-fluorobutyl)benzyl, 4-(5-chloropentyl)benzyl, 4-(6-bromohexyl)benzyl, α-(4-propylphenyl)ethyl, 4-(t-butylphenyl)benzyl, 3-(pentylphenyl)benzyl, β-(4-hexylphenyl)ethyl, 4-(propoxy)benzyl, 3-(t-butoxy)benzyl, 4-(pentyloxy)benzyl and 4-(hexyloxy)benzyl groups and the like can be exemplified.

As to the heterocyclic group formed by combining $R^1$ and $R^2$ together with the nitrogen atom being bonded thereto, with or without additional nitrogen atom or oxygen atom, 1-pyrrolidinyl, piperidino, 1-piperazinyl and morpholino groups and the like can be exemplified.

As to the above-mentioned heterocyclic group which is substituted with a $C_{1-6}$ alkyl group, a phenyl-$C_{1-6}$ alkyl group, a phenyl group, or substituted phenyl group having substituents selected from the group consisting of a $C_{1-6}$ alkyl group, a $C_{1-6}$ alkoxy group, a halogen atom and a halogen-substituted $C_{1-6}$ alkyl group, 4-methyl-1-piperazinyl, 4-ethyl-1-piperazinyl, 4-t-butyl-1-piperazinyl, 4-phenyl-1-piperazinyl, 4-benzyl-1-piperazinyl, 4-(2-methoxyphenyl)-1-piperazinyl, 4-(4-methoxyphenyl)-1-piperazinyl, 4-(4-chlorophenyl)-1-piperazinyl, 4-(2-fluorophenyl)-1-piperazinyl, 4-(4-bromophenyl)-1-piperazinyl, 4-(4-fluorophenyl)-1-piperazinyl, 4-(2-methylphenyl)-1-piperazinyl, 4-(4-ethylphenyl)-1-piperazinyl, 4-(3-trifluoromethylphenyl)-1-piperazinyl, 4-(β-phenethyl)-1-piperazinyl, 4-methylpiperidino, 4-pheneylpiperidino, 4-pentyl-1-piperazinyl, 4-hexyl-1-piperazinyl, 4-(3-phenylpropyl)-1-piperazinyl, 4-(6-pheneylhexyl)-1-piperazinyl, 4-(2-propoxyphenyl)-1-piperazinyl, 4-(4-pentyloxyphenyl)-1-piperazinyl, 4-(3-hexyloxyphenyl)-1-piperazinyl, 4-(4-butylphenyl)-1-piperazinyl, 4-(3-pentylphenyl)-1-piperazinyl, 4-(4-hexylphenyl)-1-piperazinyl, 4-[3-(2-chloroethyl)phenyl]-1-piperazinyl, 4-[4-(4-bromobutyl)phenyl]-1-piperazinyl, 4-[4-(6-fluorohexyl)phenyl]-1-piperazinyl, 3-methyl-2-morpholino, 6-phenyl-3-morpholino, 2-benzyl-3-morpholino, 5-(4-chlorophenyl)-3-morpholino, 3-methoxy-1-piperidinyl, 3-methyl-1-piperidinyl, 3-methyl-1-pyrrolidinyl, and 2-benzyl-1-pyrrolidinyl groups and the like can be exemplified.

The carboxyamide compounds represented by the above-mentioned formula (1) include some novel compounds which were found and developed by the present inventors. These compounds can be prepared by methods as disclosed in the specification of Japanese Patent Kokai (Laid-open) No. 61-151199 (1986).

Thus carboxamide compounds represented by the formula (1) can be prepared by, for example, the following method.

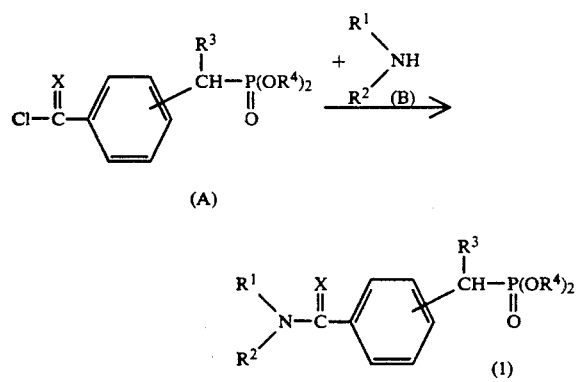

(wherein $R^1$, $R^2$, $R^3$, $R^4$ and X are the same as defined above.)

According to Reaction Scheme - 1, a carboxylic acid chloride (A) is reacted with an amine compound (B) to prepare a carboxamide compound (1).

The reaction can be carried out in a suitable solvent, in the presence of an deacidifying agent. As to the deacidifying agent, any known compounds which does not give any adverse effect may be used, for example, tertiary amines such as triethylamine, diethylaniline, N-methylmorpholine, pyridine, 4-dimethylaminopyridine and the like can preferably be exemplified. As to the solvent, an aromatic hydrocarbon such as benzene, toluene, xylene and the like; an aliphatic or cyclic ether such as diethyl ether, dimethoxyethane, tetrahydrofuran (THF), 1,4-dioxane and the like can be exemplified. Ketones such as acetone, methyl ethyl ketone, acetophenone and the like can be examplified, and halogenated hydrocarbons such as dichloromethane, chloroform, carbon tetrachloride, 1,2-dichloroethane and the like can be exemplified.

The ratio of the amount of carboxylic acid chloride (A) to the amount of amine compound (B) in the reaction is not specifically restricted, and generally, an equimolar to an excess quantity of the former may be used to the latter. Furthermore, the amount of the deacidifying agent may be preferably used in amount of an equimolar quantity to a slight excess quantity to the carboxylic acid chloride compound (A). The reaction can be proceeded either under cooling condition or room temperature or rubber heating condition, and preferably may be carried out under the temperature condition within the range from room temperature to refluxing temperature of the solvent to be used, the reaction is generally completed in about 0.5 to 10 hours.

The carboxamide compound of the formula (1) thus prepared according to the above-mentioned reaction may be isolated or purified from the reaction system by using conventional separating means, for example, solvent extraction, distillation, recrystallization, column chromatography, preparative thin layer chromatography and the like.

EXAMPLE 1

Preparation of 4-diethoxyphosphinoylmethyl-N-(4-bromo-2-cyanophenyl)benzamide 3.94 Grams (20 mM) of 2-amino-5-bromobenzonitrile, 2.22 g (22 mM) of triethylamine and 0.49 g (4 mM) of 4-diethylaminopyridine were dissolved in 40 ml of anhydrous dichloromethane. To this solution was added dropwise 40 ml of anhydrous dichloromethane solution with 5.81 g (20 mM) of 4-diethoxyphosphinoylmethylbenzoyl chloride at 0° C. with stirring. After the stirring was continued for 10 hours at room temperature, 50 ml of water was added to the reaction mixture, and the whole mixture was extracted with chloroform. The chloroform extracts were dried over anhydrous sodium sulfate and concentrated. Thus obtained residue was purified by means of a silica gel column chromatography (eluted with chloroform:ethyl acetate=1:2). The crude crystals were recrystallized from benzene-n-hexane to yield 2.94 g of 4-diethoxyphosphinoylmethyl-N-(4-bromo-2-cyanophenyl)benzamide as colorless crystals.

Melting point: 165°–166° C.

EXAMPLES 2–7

By procedure similar to that employed in Example 1, compounds of Examples 2–7 were prepared as shown in Table 1 as follows. In Table, the chemical structural formula of the compound prepared in Example 1 is also shown.

TABLE 1

| Example No. | Chemical Structural Formula | Melting point (°C.) |
|---|---|---|
| 1 | Br—(phenyl with CN)—NH—C(=O)—(phenyl)—CH$_2$—P(=O)(OC$_2$H$_5$)$_2$ | 165–166 Recrystallization solvent: Benzene-n-hexane |
| 2 | Cl—(phenyl with CN)—NH—C(=O)—(phenyl)—CH$_2$—P(=O)(OC$_2$H$_5$)$_2$ | 171–172 Recrystallization solvent: Chloroform-n-hexane |
| 3 | NC—(phenyl with Cl)—NH—C(=O)—(phenyl)—CH$_2$—P(=O)(OC$_2$H$_5$)$_2$ | 152–154 Recrystallization solvent: Benzene-n-hexane |

TABLE 1-continued

| Example No. | Chemical Structural Formula | Melting point (°C.) |
|---|---|---|
| 4 | I-C$_6$H$_3$(CN)-NH-CO-C$_6$H$_4$-CH$_2$-P(O)(OC$_2$H$_5$)$_2$ | 176–177 Recrystallization solvent: Benzene |
| 5 | NC-C$_6$H$_3$(Br)-NH-CO-C$_6$H$_4$-CH$_2$P(O)(OC$_2$H$_5$)$_2$ | 152–154 Recrystallization solvent: Benzene-n-hexane |
| 6 | Br-C$_6$H$_3$(NC)-NH-CO-C$_6$H$_4$-CH$_2$-P(O)(OC$_2$H$_5$)$_2$ | 208.5–209.5 Recrystallization solvent: Chloroform-n-hexane |
| 7 | NC-C$_6$H$_3$(I)-NH-CO-C$_6$H$_4$-CH$_2$-P(O)(OC$_2$H$_5$) | 111.5–113.5 Recrystallization solvent: Benzene-n-hexane |

In the above-mentioned specification of Japanese Patent Kokai (Laid-open) No. 61-151199 (1986), there are only disclosed that these compounds possess anti-inflammatory effect and calcium antagonizing effect, thus these compounds are useful as anti-inflammatory agents, agents for preventing and treating ischematic heart diseases such as angina pectoris, myocardial infarction, arrhythmia and the like, as well as agents for preventing and treating hypertension.

While, the pharmacological activities relating to the above-mentioned usages of these compounds are not connected at all with the pharmacological activities relating to the agents for treating hyperlipidemia according to the present invention. In fact that, the specification of the above-mentioned Japanese Patent Kokai (Laid-open) No. 61-151199 (1986) discloses that carboxamide compounds represented by the formula (1) neither possess activities for lowering the concentration of lipids in blood, nor useful as agents for treating hyperlipidemia.

The pharmaceutical composition for treating hyperlipidemia according to the present invention is considerably effective for treating and preventing various diseases of hyperlipidemia, such as hypercholesterolemia, hypertriglyceridemia, hyperphospholipidemia, hyper-free fatty acidemia and the like, on the basis of their excellent pharmacological activiries, especially effects for lowering the concentration of lipids in blood, such as effects for lowering the concentration of cholesterol in blood, effects for lowering the concentration of neutral fats in blood, effects for lowering the concentration of phospholipids in blood and the like. Furthermore, the pharmaceutical composition for treating hyperlipidemia according to the present invention is also considerably effective for preventing and treating arteriosclerosis induced by the above-mentioned diseases of hyperlipidemia.

In addition to the above, the pharmaceutical composition for treating hyperlipidemia according to the present invention is characterized in that its pharmacological activities can be prolonged for a certain length of period, as well as it has lower toxicity, thus it is quite suitable as a drug for treating the above-mentioned diseases.

The pharmaceutical composition for treating hyperlipidemia according to the present invention contains, as the essential factor, at least one carboxamide compound represented by the above-mentioned formula (1). Generally, said pharmaceutical compositions are prepared in various forms of pharmaceutical preparations depend on methods of administration, by admixing the carboxyamide compound with none toxic pharmaceutically acceptable carriers which are commonly used, thus prepared pharmaceutical composition is administered to patients of hyperlipidemia and/or patients of arteriosclerosis as a treating agent, or administered as an agent for preventing these diseases.

As to the pharmaceutically acceptable carriers, which are commonly used depend on various preparation forms, any type of diluents or solvents, fillers, bulking agents, binding agents, dispersing agents, disintegrating agents, surface active agents, lubricants, excipients and wetting agents can be examplified. Furthermore, if necessary, commonly used dissolving adjuvants, buffering agents, preservatives, coloring agents, perfumes, seasoning agents, and the like may also be added to the pharmaceutical preparations.

Administration unit forms of pharmaceutical compositions according to the present invention are not specifically restricted and can be selected from widely, depend on various therapeutical purposes, for example, oral administration preparations such as tablets, tablets, capsules, granules, pills, syrups, liquids, emulsions, suspensions and the like, parenteral administration preparations such as injection preparations (subcutaneously, intravenously, intramuscularly, intraperitoneally and the like) and suppositories. Among these preparations, oral administration preparations are particularly preferable.

The above-mentioned various forms of pharmaceutical preparations can be prepared by usual methods. For example, in preparing the oral administration preparations, such as tablets, capsules, granules and pills, they can be prepared by using excipients for example, white sugar, lactose, glucose, starch, mannitols; binding agents for example, syrup, gum arabi, sorbitol, tragacanth gum, methyl cellulose, polyvinyl pyrrolidone and the like; disintegrating agents for example, starch, carboxymethyl cellulose and its calcium salt, microcrystalline cellulose, polyethylene glycols and the like; lubricants for example, talc, magnesium stearate, calcium stearate, silica and the like; wetting agents for example, sodium laurate, glycerol and the like, by means of conventional methods.

In preparing injection preparations, liquids, emulsions, suspensions and syrup preparations, they can be prepared, by means of conventional methods and suitably using solvents for example, ethyl alcohol, isopropyl alcohol, propylene glycol, 1,3-butylene glycol, polyethylene glycols, castor oil and the like, for dissolving the active ingredient; surface active agents for example fatty acid esters of sorbitol, fatty acid esters of polyoxyethylene sorbitol, esters of polyolyethylene, polyoxyethylene ether of hydrogenated castor oil, lecithin and the like; suspending agents for example cellulose derivatives such as sodium carboxymethyl cellulose, methyl cellulose and the like, and natural gums such as gum tragacanth, gum arabi and the like; preservatives for example esters of paraoxybenzoic acid, benzalkonium chloride, sorbitan fatty acid salts and the like.

In preparing suppositories, they can be prepared by means of conventional methods and by using excipients such as polyethylene glycols, lanolin, coconut oil and the like.

Dosages of the desired pharmaceutical composition for treating hyperlipidemia according to the present invention may suitably be selected depending upon methods of administration, form of the preparations, age of the patient, body weight of the patient, sensitivities of the patient, conditions of the disease, and are not specifically restricted. Generally, the amount of the active ingredient to be contained in each of these pharmaceutical compositions may be in about 0.05 to 80 mg, preferably about 0.1 to 50 mg/kg of the body weight per day. Of cause, the amount of the active ingredient may be administered in an amount without the above-mentioned range.

The present invention will be explained in more detail by illustrating the following examples of pharmaceutical preparations for treating hyperlipidemia, and pharmacological test results of the active ingredient contained in the pharmaceutical compositions.

EXAMPLE OF PHARMACEUTICAL PREPARATION - 1

Preparation of Tablets - (1)

Tablets (1,000 tablets) each of which containing 250 mg of 4-diethoxyphophinoylmethyl-N-(4-chlorophenyl)benzamide (hereinafter referred to as "Compound A") as the active ingredient were prepared by the following formulation.

| Ingredients | Amount (g) |
| --- | --- |
| Compound A | 250 |
| Lactose (Japanese Pharmacopoeia grade) | 33.3 |
| Corn starch | 16.4 |
| (Japanese Pharmacopoeia grade) | |
| Calcium carboxymethyl cellulose | 12.8 |
| (Japanese Pharmacopoeia grade) | |
| Methyl cellulose | 6.0 |
| (Japanese Pharmacopoeia grade) | |
| Magnesium stearate | 1.5 |
| (Japanese Pharmacopoeia grade) | |
| Total amount | 320 g |

In accordance with the above-mentioned formulation, Compound A, lactose, corn starch and calcium carboxymethyl cellulose were thoroughly admixed together, then the mixture was shaped into granular form by using an aqueous solution of methyl cellulose, then thus obtained granules were passed through a sieve (No. 24), the granules being passed were mixed with magnesium stearate and then pressed into tables form.

EXAMPLE OF PHARMACEUTICAL PREPARATION - 2

Preparation of Capsules - (1)

Hard gelatin capsules (1,000 capsules) each of which containing 4-diethoxyphophinoylmathyl-N-benzyl-N-(4-chlorophenyl)benzamide (hereinafter referred to as "Compound B") as the active ingredient were prepared by the following formulation.

| Ingredients | Amount (g) |
| --- | --- |
| Compound B | 250 |
| Crystalline cellulose | 30 |
| (Japanese Pharmacopoeia grade) | |
| Corn starch | 17 |
| (Japanese Pharmacopoeia grade) | |
| Talc (Japanese Pharmacopoeia grade) | 2 |
| Magnesium stearate | 1 |
| (Japanese Pharmacopoeia grade) | |
| Total amount | 300 g |

Each of the above-mentioned ingredients were finely pulverized, then admixed thoroughly so as to form a uniform mixture. The mixture was filled in a gelatin capsule for oral administration having the desired size to prepare the capsule preparation.

EXAMPLE OF PHARMACEUTICAL PREPARATION - 3

Preparation of Granules - (1)

Granules (1,000 g), containing 500 mg/g of 4-diethoxyphosphinoylmethyl-N-phenylbenzamide (hereinafter referred to as "Compound C") as the active ingredient was prepared by the following formulation.

| Ingredients | Amount (g) |
| --- | --- |
| Compound C | 500 |
| Corn starch | 250 |
| (Japanese Pharmacopoeia grade) | |
| Lactose | 100 |
| (Japanese Pharmacopoeia grade) | |
| Crystalline cellulose | 100 |
| (Japanese Pharmacopoeia grade) | |
| Calcium carboxymethyl cellulose | 40 |
| (Japanese Pharmacopoeia grade) | |
| Hydroxypropyl cellulose | 10 |
| (Japanese Pharmacopoeia grade) | |
| Total amount | 1,000 g |

In accordance with the above-mentioned formulation, Compound C, corn starch, lactose, crystalline cellulose and calcium carboxymethyl cellulose were admixed thoroughly, then an aqueous solution of hydroxypropyl cellulose was added to the mixture and kneaded, they by using a extruding-granulating machine to prepare granules, and dried at 50° C. for 2 hours to prepare the desired granular preparation.

EXAMPLE OF PHARMACEUTICAL PREPARATION - 4

Preparation of Tablets - (2)

Tablets (1,000 tablets) each of which containing 250 mg of 4-diethoxyphosphinoylmethyl-N-(4-bromo-2-cyanophenyl)benzamide (hereinafter referred to as "Compound D") as the active ingredient were prepared by the following formulation.

| Ingredients | Amount (g) |
| --- | --- |
| Compound D | 250 |
| Lactose | 33.3 |
| (Japanese Pharmacopoeia grade) | |
| Corn starch | 16.4 |
| (Japanese Pharmacopoeia grade) | |
| Calcium carboxymethyl cellulose | 12.8 |
| (Japanese Pharmacopoeia grade) | |
| Methyl cellulose | 6.0 |
| (Japanese Pharmacopoeis grade) | |
| Magnesium stearate | 1.5 |
| (Japanese Pharmacopoeia grade) | |
| Total amount | 320.0 g |

In accordance with the above-mentioned formulation, Compound D, lactose, corn starch and calcium carboxymethyl cellulose were thoroughly admixed together, the mixture thus obtained was shaped into granular form by using an aqueous solution of methyl cellulose, then the granules were passed through a sieve (No. 24), and the granules being passed were mixed with magnesium stearate and then pressed into tablets form.

EXAMPLE OF PHARMACEUTICAL PREPARATION - 5

Preparation of Capsules - (2)

Hard gelatin capsules (1,000 capsules) each of which containing 4-diethoxyphosphinoylmethyl-N-(2-chloro-4-cyanophenyl)benzamide (hereinafter referred to as "Compound E") as the active ingredient were prepared by the following formulation.

| Ingredients | Amount (g) |
| --- | --- |
| Compound E | 250 |
| Crystalline cellulose | 30 |
| (Japanese Pharmacopoeia grade) | |
| Corn starch | 17 |
| (Japanese Pharmacopoeia grade) | |
| Talc | 2 |
| (Japanese Pharmacopoeia grade) | |
| Magnesium stearate | 1 |
| (Japanese Pharmacopoeia grade) | |
| Totala amount | 320 g |

In accordance with the above-mentioned formulation, each of the ingredients was finely pulverized, then they were admixed thoroughly so as to form a uniform mixture. The mixture was filled in a gelatin capsule for oral administration, having the desired size, so as to prepare capsule preparation.

EXAMPLE OF PHARMACEUTICAL PREPARATION - 6

Preparation of Granules - (2)

Granules (1,000 g), containing 500 mg of 4-diethoxyphosphinoylmethyl-N-(2-bromo-4-cyanophenyl)benzamide (hereinafter referred to as "Compound F") as the active ingredient were prepared by the following formula.

| Ingredient | Amount (g) |
| --- | --- |
| Compound F | 500 |
| Corn starch | 250 |
| (Japanese Pharmacopoeia grade) | |
| Lactose | 100 |
| (Japanese Pharmacopoeia grade) | |
| Crystalline cellulose | 100 |
| (Japanese Pharmacopoeia grade) | |
| Calcium carboxymethyl cellulose | 40 |
| (Japanese Pharmacopoeia grade) | |
| HYdroxypropyl cellulose | 10 |
| (Japanese Pharmacopoeia grade) | |
| Total amount | 1,000 g |

In accordance with the above-mentioned formulation, Compound F, corn starch, lactose, crystalline cellulose and calcium carboxylmethyl cellulose were admixed thoroughly, then an aqueous solution of hydroxypropyl cellulose was added to the mixture and the whole mixture was kneaded, then by using a extruding-granulating machine to prepare granules, and the granules were dried at 50° C. for 2 hours to prepare the desired granular preparation.

PHARMACOLOGICAL TESTS

The following pharmacological tests were conducted to show the effectiveness of carboxyamide compounds represented by the formula according to the present invention.

In conducting the pharmacological tests, the following carboxamide compounds were used as test compounds.

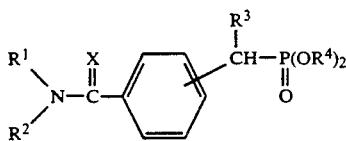
| Test compound No. | X | Substituted position of the sidechain in the phenyl ring | R¹ | R² | R³ | R⁴ |
|---|---|---|---|---|---|---|
| 1. | O | 4 | H | 4-Cl-C₆H₄- | H | Ethyl |
| 2. | O | 4 | C₆H₅-CH₂- | 4-Cl-C₆H₄- | H | Ethyl |
| 3. | O | 4 | C₆H₅-CH₂- | 5-Cl-2-CH₃-C₆H₃- | H | Ethyl |
| 4. | O | 4 | C₆H₅-CH₂- | 3,4-Cl₂-C₆H₃- | H | Ethyl |
| 5. | O | 4 | H | 3,4-Cl₂-C₆H₃- | H | Ethyl |
| 6. | O | 4 | H | C₆H₅- | H | Ethyl |
| 7. | O | 4 | CH₃- | C₆H₅- | H | Ethyl |
| 8. | O | 4 | H | 4-Br-C₆H₄- | H | Ethyl |
| 9. | O | 4 | H | 4-Cl-3-CF₃-C₆H₃- | H | Ethyl |
| 10. | O | 4 | C₆H₅-CH₂- | 4-O₂N-C₆H₄- | H | Ethyl |

-continued
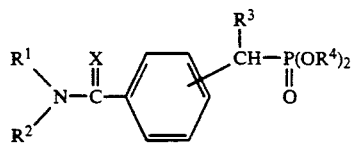
| Test compound No. | X | Substituted position of the sidechain in the phenyl ring | R¹ | R² | R³ | R⁴ |
|---|---|---|---|---|---|---|
| 11. | O | 4 | H | C₆H₅—CH₂CH₂— | H | iso-Propyl |
| 12. | O | 4 | C₆H₅—CH₂— | 4-F₃C-C₆H₄— | H | Ethyl |
| 13. | O | 4 | H | 4-F₃C-C₆H₄— | H | Ethyl |
| 14. | O | 4 | CH₃— | 4-Cl-C₆H₄— | H | Ethyl |
| 15. | O | 4 | cyclopentyl | 4-Cl-C₆H₄— | H | Ethyl |
| 16. | O | 4 | H | 4-I-C₆H₄— | H | Ethyl |
| 17. | O | 4 | 4-Cl-C₆H₄—CH₂— | 3,4-Cl₂-C₆H₃— | H | Ethyl |
| 18. | O | 4 | H | 4-O₂N-C₆H₄— | H | Ethyl |
| 19. | O | 4 | H | 4-NC-C₆H₄— | H | Ethyl |
| 20. | O | 4 | H | 4-F-C₆H₄— | H | Ethyl |
| 21. | O | 4 | 4-Cl-C₆H₄—CH₂— | 4-Cl-C₆H₄— | H | Ethyl |

-continued
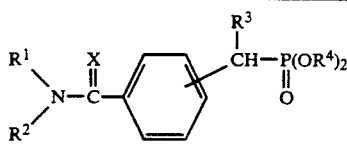
| Test compound No. | X | Substituted position of the sidechain in the phenyl ring | R¹ | R² | R³ | R⁴ |
|---|---|---|---|---|---|---|
| 22. | O | 4 | H | H₃C-⟨C₆H₄⟩- | H | Ethyl |
| 23. | O | 4 | H | H₃CO-⟨C₆H₄⟩- | H | Ethyl |
| 24. | O | 3 | CH₃OCO-⟨C₆H₄⟩- | ⟨C₆H₅⟩- | H | Ethyl |
| 25. | O | 2 | CH₃O-⟨C₆H₄⟩- | NC-⟨C₆H₄⟩-CH₂- | H | Ethyl |
| 26. | O | 4 | n-Hexyl- | H | CH₃- | iso-Propyl |
| 27. | O | 4 | F₃C-⟨C₆H₄⟩- | H | H | Ethyl |
| 28. | O | 4 | HO-⟨C₆H₄⟩- (OH) | H | H | Ethyl |
| 29. | O | 4 | 2,6-Cl₂-⟨C₆H₃⟩- | H | H | ⟨C₆H₅⟩- |
| 30. | O | 4 | 3,4-(H₃CO)₂-⟨C₆H₃⟩-CH₂CH₂- | H | H | Ethyl |
| 31. | O | 4 | (C₆H₅)₂CHCH₂CH₂- | H | H | Ethyl |

-continued

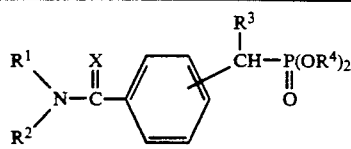

| Test compound No. | X | Substituted position of the sidechain in the phenyl ring | R¹ | R² | R³ | R⁴ |
|---|---|---|---|---|---|---|
| 32. | O | 4 | iso-Propyl- | phenyl | H | Ethyl |
| 33. | O | 4 | n-Octyl- | phenyl | H | Ethyl |
| 34. | O | 4 | n-Octyl- | phenyl | n-Octyl | Ethyl |
| 35. | O | 4 | cyclohexyl- | phenyl | H | Ethyl |
| 36. | O | 4 | phenyl- | phenyl | H | Ethyl |
| 37. | O | 4 | H₃C-C₆H₄-CH₂- | phenyl | H | Ethyl |
| 38. | O | 4 | H₃CO-C₆H₄-CH₂- | phenyl | H | Ethyl |
| 39. | O | 4 | O₂N-C₆H₄-CH₂- | phenyl | H | Ethyl |
| 40. | O | 4 | F₃C-C₆H₄-CH₂- | phenyl | H | Ethyl |
| 41. | O | 4 | F-C₆H₄-CH₂- | phenyl | H | Ethyl |
| 42. | O | 4 | C₆H₅-CH₂CH₂- | phenyl | H | Ethyl |

-continued

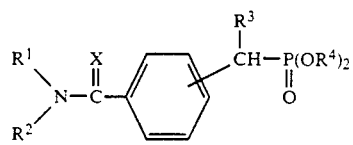

| Test compound No. | X | Substituted position of the sidechain in the phenyl ring | R¹ | R² | R³ | R⁴ |
|---|---|---|---|---|---|---|
| 43. | O | 4 | CH₃— | phenyl-CH₂— | H | Ethyl |
| 44. | O | 4 | iso-Propyl- | phenyl-CH₂— | H | Ethyl |
| 45. | O | 4 | cyclohexyl- | phenyl-CH₂— | H | Ethyl |
| 46. | O | 4 | 4-H₃C-C₆H₄— | phenyl-CH₂— | H | Ethyl |
| 47. | O | 4 | 2-F-C₆H₄— | phenyl-CH₂— | H | Ethyl |
| 48. | O | 4 | 4-H₃CO-C₆H₄— | phenyl-CH₂— | H | Ethyl |
| 49. | O | 4 | 4-NC-C₆H₄— | phenyl-CH₂— | H | Ethyl |
| 50. | O | 4 | 3-F₃C-C₆H₄— | phenyl-CH₂— | H | Ethyl |
| 51. | O | 4 | 3-F₃C-C₆H₄— | phenyl-CH₂— | phenyl-CH₂— | Ethyl |
| 52. | O | 4 | 3,4,5-(H₃CO)₃-C₆H₂— | phenyl-CH₂— |  | Ethyl |

-continued

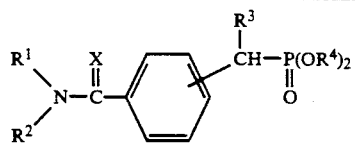

| Test compound No. | X | Substituted position of the sidechain in the phenyl ring | R¹ | R² | R³ | R⁴ |
|---|---|---|---|---|---|---|
| 53. | O | 4 | 3,4-dimethoxyphenyl (H₃CO, H₃CO substituents) | benzyl (–CH₂–phenyl) | H | Ethyl |
| 54. | O | 4 | benzyl (–CH₂–phenyl) | benzyl (–CH₂–phenyl) | H | Ethyl |
| 55. | O | 4 | 2-bromophenyl | H | H | Ethyl |
| 56. | O | 4 | H₃C–N(piperidine) | | H | Ethyl |
| 57. | O | 4 | 2-methylphenyl-N(piperidine) | | H | Ethyl |
| 58. | O | 4 | 4-chlorophenyl-N(piperidine) | | H | Ethyl |
| 59. | O | 4 | 4-methoxyphenyl-N(piperidine) | | H | Ethyl |
| 60. | O | 4 | 3-trifluoromethylphenyl-N(piperidine) | | H | Ethyl |
| 61. | O | 4 | phenyl–CH₂–N(piperidine) | | H | Ethyl |
| 62. | O | 4 | phenyl–CH₂CH₂– | benzyl (–CH₂–phenyl) | H₃C– | Ethyl |
| 63. | O | 4 | n-Hexyl- | H | H₃C– | Ethyl |

-continued
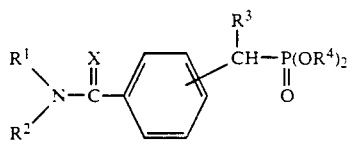
| Test compound No. | X | Substituted position of the sidechain in the phenyl ring | R¹ | R² | R³ | R⁴ |
|---|---|---|---|---|---|---|
| 64. | O | 3 | phenyl | H | H | Ethyl |
| 65. | O | 4 | benzyl (C₆H₅CH₂—) | phenyl | H | Ethyl |
| 66. | O | 4 | 2-COOH-phenyl | H | H | Ethyl |
| 67. | S | 4 | phenyl | H₃C— | H | Ethyl |
| 68. | S | 4 | benzyl (C₆H₅CH₂—) | H₃C— | H | Ethyl |
| 69. | S | 4 | benzyl (C₆H₅CH₂—) | benzyl (C₆H₅CH₂—) | H | Ethyl |
| 70. | S | 4 | phenyl | H | H | Ethyl |
| 71 | O | 4 | 2-CN-5-Br-phenyl | H | H | Ethyl |
| 72 | O | 4 | 2-CN-5-Cl-phenyl | H | H | Ethyl |
| 73 | O | 4 | 3-Cl-4-CN-phenyl | H | H | Ethyl |

-continued

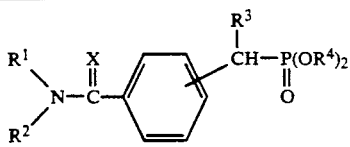

| Test compound No. | X | Substituted position of the sidechain in the phenyl ring | R¹ | R² | R³ | R⁴ |
|---|---|---|---|---|---|---|
| 74 | O | 4 | 2-CN, 5-I phenyl | H | H | Ethyl |
| 75 | O | 4 | 2-Br, 5-CN phenyl | H | H | Ethyl |
| 76 | O | 4 | 2-NC, 5-Br phenyl | H | H | Ethyl |
| 77 | O | 4 | 2-I, 5-NC phenyl | H | H | Ethyl |

(A) PHARMACOLOGIC TEST-1

Test for determining antilipotropic effect in Triton WR-1339-induced hyperlipidemia in rat Wistar-strain male rats of 5–9 week age were used as test animals. One test group consisting of six (6) rats. 400 Milligrams/kg of Triton WR-1339 (a tradename of an oxyethylated tertiary octylphenol formaldehyde polymer, manufacture bu Rohm & Haas Co., U. S. A.) was administered to the tail vein of the test rat, then 3 to 6 hours after the administration, 50 mg/kg of each of the test compounds which was suspended in 0.5%-CMC-Na aqueous solution was orally administered to the rat. Similar to above, to each of six (6) rats in control group was administered with Triton WR-1339, and further orally administered with 0.5% CMC-Na aqueous solution without containing each one of the test compounds.

24 Hours and 48 hours after the administration with Triton WR-1339, the blood samples were taken from each of the test rats, then the total serum cholesterol and serum triglycerides were respectively determined by using a test reagent of Cholesterol C-Test Wako, and a test reagent of Triglyceride G-Test Wako (both are manufactured by Wako Pure Chemicals Co., Ltd.).

Lowering effect of total serum cholesterol and of serum trigricerides of the test group at each of 24 hours and 48 hours after the administration of Triton WR-1339 were calculated, in terms of lowering ratio (%), from the formula on the basis of the total serum cholesterol and serum triglyceride of control group as follows.

$$\text{Lowering ratio (\%)} = \frac{[a] - [b]}{[a]}$$

(wherein

[a] is a determined value obtained from the control group, and

[b] is a determined value obtained from the test group).

In conducting the test, rats used as the test animals were abstained from food before the administration with Triton WR-1339 through the final blood sampling, while water was given freely.

The results are shown in Table 1 and 2 in which Clinofibrate (i.e., 2,2-[cyclohexylidenbis(4,1-phenylenoxy)bis[2-methylbutanoic acid]) was used as the reference compound.

Table 1 shows the lowering ratio performed by test compounds to the total serum cholesterol after the administration of Triton WR-1339, while Table 2 shows the lowering ratio performed by test compounds to the serum triglycerides after the administration of Triton WR-1339.

As can be seen from the data shown in Tables 1 and 2, the total serum cholesterol (Table 1) and serum triglycerides (Table 2) can be remarkably lowered by using carboxamide compounds according to the present invention, thus carboxamide compounds according to the present invention possess strong serum lipids lowering activities. Furthermore, these carboxamide compounds prolong their pharmacological activities for certain length of period, thus useful agents for preventing and treating hyperlipidemia for clinical uses can be expected by using these carboxamide compounds according to the present invention.

TABLE 1

Lowering effects to the total serum cholesterol after Triton WR-1339 was administered

| Test compound No. | After Triton WR-1339 was administered | |
|---|---|---|
| | 24 hours | 48 hours |
| 1. | 51.6 | 67.9 |
| 2. | 42.5 | 69.4 |
| 3. | 11.0 | 16.9 |
| 4. | 26.4 | 56.3 |
| 5. | 17.4 | 49.6 |
| 6. | 49.1 | 58.9 |
| 7. | 38.0 | 50.0 |
| 8. | 52.2 | 63.6 |
| 9. | 11.7 | 42.3 |
| 10. | 0 | 16.1 |
| 11. | 13.5 | 32.6 |
| 12. | 36.9 | — |
| 13. | 33.7 | 64.4 |
| 14. | 29.3 | 49.4 |
| 15. | 9.8 | 22.6 |
| 16. | 64.0 | 75.1 |
| 17. | 27.8 | 64.4 |
| 18. | 32.7 | 37.5 |
| 19. | 60.6 | 63.6 |
| 20. | 27.0 | 55.1 |
| 21. | 15.9 | 52.3 |
| 22. | 6.9 | 29.0 |
| 23. | 17.3 | 32.5 |
| Clinofibrate (Reference compound) | 9.8 | 1.9 |

TABLE 2

Lowering effects to the serum triglycerides after Triton WR-1339 was administered.

| Test compound No. | After Triton WR-1339 was administered | |
|---|---|---|
| | 24 hours | 48 hours |
| 1. | 85.3 | 95.9 |
| 2. | 69.3 | 94.5 |
| 3. | 43.4 | 27.6 |
| 4. | 61.4 | 89.1 |
| 5. | 32.8 | 85.4 |
| 6. | 73.8 | 90.8 |
| 7. | 64.9 | 75.3 |
| 8. | 86.8 | 92.5 |
| 9. | 11.3 | 68.4 |
| 10. | 26.9 | 68.7 |
| 11. | 0 | 56.8 |
| 12. | 60.4 | 83.9 |
| 13. | 73.9 | 95.4 |
| 14. | 46.0 | — |
| 15. | 23.0 | 55.8 |
| 16. | 94.1 | 95.3 |
| 17. | 56.8 | 94.1 |
| 18. | 54.4 | 74.9 |
| 19. | 90.5 | 94.7 |
| 20. | 57.3 | 90.5 |
| 21. | 47.9 | 89.1 |
| 22. | 38.6 | 28.1 |
| 23. | 25.5 | 27.6 |
| Clinofibrate (Reference compound) | 13.6 | 1.1 |

(B) Pharmacological Test-2

Test for determining inhibitory effect in biosynthetic pathway of cholesterol

Each one of the test compounds was added to rat liver microsomes fraction (containing 0.2 mg of protein) and soluble fraction (containing 2 mg of protein), then the volume of the mixture was adjusted to 100 microliters by adding 0.1 M-potassium phosphate buffer solution (pH 7.4), then this mixture was incubated at 37° C. for 10 minutes.

After the incubation, the reaction was started by adding 200 microliters of a solution containing 1 mM ATP, 10 mM glucose-1-phosphate, 6 mM glutathione, 6 mM MgCl$_2$, 40 micromoles CoA, 0.25 mM AND, 0.25 mM NADP, and 1 mM [1—$^{14}$C] sodium acetate (3.0 mCi/mM).

The whole mixture was incubated at 37° C. for 90 minutes, then the reaction was terminated by adding 1 mM of 15%-KOH (a 95% ethanol solution), next 2 mg of cholesterol was added thereto, saponified at 75° C. for 1 hour, and cholesterol was extracted with petroleum ether, the extract was concentrated to dryness. To the residue thus obtained was added with 2.5 ml of a mixture of acetone-diethyl ether (1:1) and 2.5 ml of 1%-digitonin (a 50% ethanol solution), then this solution was allowed to stand for 1 hour in cooling condition by using ice-water to precipitate cholesterol. The precipitate was washed with acetone, a mixture of acetonediethyl ether (1:1) and diethyl ether in this order, then the radioactivity of the residue was measured by using a liquid scintillation counter.

Control test was also conducted by the procedures similar to those mentioned above in the test group, except that each one of the test compounds was not used.

Inhibitory effect in biosynthetic pathway of cholesterol performed by each one of the test compounds was calculated, in terms of inhibitory ratio (%), from the formula on the basis of the radioactivity of the control group as follows:

$$\text{Inhibitory ratio (\%)} = \frac{[c] - [d]}{[c]}$$

(wherein
[c] is a radioactivity of the control group, and
[d] is a radio activity of the test group).

The results are shown in Tables 3 and 4. Table 3 shows inhibitory ratios of carboxamide compounds represented by the formula (1) wherein X=O, and Table 4 shows inhibitory ratios of carboxamide compounds represented by the formula (1) wherein X=S.

TABLE 3

Inhibitory effect to choleresterol biosynthesis

| Test compound No. | Inhibitory ratio of cholesterol biosynthesis ($10^{-4}$ M) | Test compound No. | Inhibitory ratio of cholesterol biosynthesis ($10^{-4}$ M) |
|---|---|---|---|
| 1. | 56.6 | 40. | 91.6 |
| 2. | 88.0 | 41. | 84.2 |
| 3. | 87.1 | 42. | 86.7 |
| 4. | 95.2 | 43. | 23.8 |
| 7. | 65.8 | 44. | 46.2 |
| 10. | 75.6 | 45. | 76.9 |
| 11. | 67.4 | 46. | 59.1 |
| 22. | 32.2 | 47. | 67.2 |
| 24. | 21.6 | 48. | 63.7 |
| 25. | 20.1 | 49. | 75.2 |
| 26. | 67.4 | 50. | 78.2 |
| 27. | 36.2 | 51. | 70.4 |
| 28. | 22.1 | 52. | 65.6 |
| 29. | 35.8 | 53. | 59.0 |
| 30. | 28.9 | 54. | 69.7 |
| 31. | 65.4 | 55. | 57.1 |
| 32. | 36.4 | 56. | 23.6 |

TABLE 3-continued

Inhibitory effect to choleresterol biosynthesis

| Test compound No. | Inhibitory ratio of cholesterol biosynthesis ($10^{-4}$ M) | Test compound No. | Inhibitory ratio of cholesterol biosynthesis ($10^{-4}$ M) |
| --- | --- | --- | --- |
| 33. | 89.6 | 57. | 41.9 |
| 34. | 85.2 | 58. | 58.4 |
| 35. | 39.2 | 59. | 55.1 |
| 36. | 61.1 | 60. | 24.9 |
| 37. | 82.8 | 61. | 58.3 |
| 38. | 85.2 | 62. | 80.2 |
| 39. | 74.6 | 63. | 58.9 |

TABLE 4

| Test compound No. | Inhibitory ratio of cholesterol biosynthesis ($10^{-4}$ M) |
| --- | --- |
| 67. | 32.5 |
| 68. | 57.2 |
| 69 | 85.3 |

(C) Pharmacological Test-3

Test for determining inhibitory effect in the enzymatic activities of acyl-CoA:cholesterol acyltranferase (ACAT)

50 Microliters of each one of the test compounds was added to rat liver microsomes fraction (containing 0.4 mg of protein) of which volume was adjusted to 150 microliters by adding 0.15 M-potassium phosphate buffer solution (pH 7.4), then the mixture was incubated at 37° C. for 10 minutes. After the incubation, the reaction was started by adding 50 microliters of 0.15 M-potassium phosphate buffer solution (pH 7.4) containing 18 nM $[1-^{14}C]$ oleoyl-CoA (10 mCi/mM) and 0.6 mg BSA (bovine serum albumin) at 37° C. for 2 minutes. The reaction was terminated by adding 1 ml of ethanol, then 4 ml of n-hexane was added and shaken, then the n-hexane layer (upper layer) was concentrated to the volume of 3 ml under nitrogen gas stream, thus obtained cholesteryl oleate was isolated by means of a silica gel thin chromatography [developing solvent=petroleum ether: diethyl ether (95:5)] and the radioactivity was measured by using a liquid scintillation counter.

Control test was also conducted by the procedures similar to those mentioned above in the test group, except that each one of the test compounds was not used.

Inhibitory effect in the enzymatic activities of acyl-CoA:cholesterol acyltransferase (ACAT) performed by each one of the test compounds was calculated, in terms of inhibitory ratio (%), from the formula on the basis of the radioactivity of the control group as follows:

$$\text{Inhibitory ratio (\%)} = \frac{[e] - [f]}{[e]}$$

(wherein

[e] is a radioactivity of the control group, and

[f] is a radioactivity of the test group). The results are shown in Tables 5 and 6. Table 5 shows inhibitory ratios of carboxamide compounds represented by the formula (1) wherein X=O, and Table 6 shows inhibitory ratio of carboxamide compound represented by the formula (1) wherein X=S.

TABLE 5

Inhibitory effect to ACAT

| Test compound No. | Inhibitory effect to ACAT ($10^{14}$ M) | Test compound No. | Inhibitory effect to ACAT ($10^{-4}$ M) |
| --- | --- | --- | --- |
| 64. | 37.6 | 65. | 87.7 |
| 26. | 88.9 | 41. | 84.0 |
| 6. | 71.1 | 2. | 91.4 |
| 1. | 79.2 | 10. | 69.4 |
| 27. | 39.5 | 50. | 84.8 |
| 5. | 76.7 | 4. | 96.2 |
| 29. | 73.9 | 3. | 88.7 |
| 11. | 83.3 | 52. | 60.5 |
| 31. | 87.7 | 58. | 56.6 |
| 7. | 33.7 | 63. | 88.9 |
| 32. | 20.1 | 66. | 26.0 |
| 36. | 63.1 | | |

TABLE 6

Inhibitory effect to ACAT

| Test compound No. | Inhibitory effect to ACAT ($10^{-4}$ M) |
| --- | --- |
| 70. | 39.4 |

(D) Pharmacological Test-4

Test for determining serum lipids lowering effect to Streptozotocin-induced diabetes in rat Wistar-strain male rats of 7 week age were used as test animals. One test group consisting of six (6) rats. 100 Milligrams/kg of Streptozocin was administered to the tail vein of the test rat, then 4th day after the administration with Streptozocin, 25 mg/kg of each of the test compounds which was suspended in 0.5%-CMC-Na aqueous solution was orally administered to the rat. Similar to the test group, to each of six (6) rats in control group was administered with Streptozocin, and further orally administered with 0.5%-CMC-Na aqueous solution without containing each of the test compounds.

4 Hours after the administration of each of the test compounds, the blood sample was taken from each of the test rats, and serum triglycerids was measured by using a test reagent of Triglyceride G-Test Wako (manufactured by Wako Pure Chemicals, Co., Ltd.).

The results are shown in Table 7 as follows.

TABLE 7

| Test compound No. | Serum triglyceride (mg/dl) |
| --- | --- |
| 8. | 471 |
| Clinofibrate (Reference compound) | 2,067 |

As can be seen from the data shown in Table 7, a carboxamide compound represented by the formula (1) according to the present invention possesses excellent serum lipids lowering effects as compared with that of shown by reference compound.

(D) Pharmacological Test-5

Increasing rate (%) of plasma high density lipoprotein cholesterol (HDLC) concentration which is performed by a carboxamide compound of the general formula (I) of the present invention was conducted as follows.

Test Method

Seven-week-old male Wistar rats were used.

The test compound was orally administered for 2 days at a daily dose of 300 mg/kg body weight to each of six (6) rats in test group. The dosing vehicle was 0.5% sodium carboxylmethylcellulose solution, and the dosing volume was 5 ml/kg body weight.

Similar to the procedures taken to the rats in the test group, to each one of six (6) rats in control group was orally administered 0.5% sodium carboxymethylcelluose solution only.

On day 2, after fasting for 20 hours, blood was drawn from the jagular sinus with a heparinized syringe. Plasma was obtained by centrifugation.

Plasma HDLC was determined after precipitation of other lipid fraction with heparin and $Ca^{2+}$ by using HDL-C Kit-N (manufactured by Hihon Shoji Kabushiki Kaisha).

Increasing rate (%) of plasma HDLC concentration performed by a test compound was calculated from the formula as follows:

$$\text{Increasing rate (\%)} = \frac{[\text{Plasma } HDLC \text{ concentration of test group}]}{[\text{Plasma } HDLC \text{ concentration of test group}]} \times 100$$

The results are shown in Table 8 as follows.

TABLE 8

| Test compound No. | Increasing rate (%) of high density lipids concentration in the serum |
|---|---|
| 71 (Compound of Example 1) | 193 |
| 72 (Compound of Example 2) | 196 |
| 73 (Compound of Example 3) | 187 |
| 74 (Compound of Example 4) | 187 |
| 75 (Compound of Example 5) | 222 |
| 76 (Compound of Example 6) | 111 |
| 77 (Compound of Example 7) | 184 |

(F) Pharmacological Test-5

Acute toxicity test

Each of carboxamide compounds represented by the formula (1), which is the active ingredient contained in pharmaceutical composition according to the present invention, was suspended in 5%-CMC-Na aqueous solution and administered orally to Wistar-strain male rats of 7 week age (one test group consisting of 6 rats) so as to observe the acute toxicity of each of the carboxamide compounds.

For examples, the test conducted by using 2 g/kg of Test compound No. 2 indicated in Table 1 showed not any lathal case at all. Thus, $LD_{50}$ value of Test compound No. 2 is considered to higher than 2 kg/kg. Thus, carboxamide compounds represented by the formula (1) according to the present invention can be said as quite safety compounds.

What is claimed is:

1. A method for treating hyperlipidemia comprising administering, to a host afflicted with hyperlipidemia, an effective hyperlipidemia treating amount of a carboxamide compound represented by the following formula:

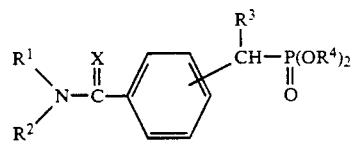

wherein $R^1$ and $R^2$ each represents hydrogen, $C_{1-15}$ alkyl, $C_{3-8}$ cycloalkyl, diphenyl-$C_{1-6}$ alkyl, or the following formula:

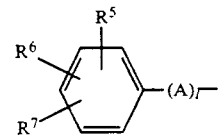

wherein $R^5$, $R^6$ and $R^7$ each represents hydrogen, halogen, nitro, $C_{1-6}$ alkoxy, $C_{1-6}$ alkoxy-carbonyl, $C_{1-6}$ alkyl, halogen-substituted $C_{1-6}$ alkyl, cyano, carbonyl or hydroxyl; A represents $C_{1-4}$ alkylene; and l represents 0 or 1; wherein $R^1$ and $R^2$ together with the nitrogen atom to which they are attached form a heterocyclic group or a heterocyclic group containing additional heteroatom(s) selected from the group consisting of a nitrogen atom and an oxygen atom, wherein said heterocyclic group is unsubstituted or substituted with $C_{1-6}$ alkyl, phenyl-$C_{1-6}$ alkyl, phenyl, or substituted phenyl having substituent(s) selected from the group consisting of the group consisting of $C_{1-6}$ alkyl, $C_{1-6}$ alkoxy, halogen and halogen-substituted $C_{1-6}$ alkyl;

$R^3$ represents hydrogen, $C_{1-15}$ alkyl or phenyl-$C_{1-6}$ alkyl; $R^4$ represents $C_{1-6}$ alkyl or phenyl; and X represents oxygen or sulfur.

2. The method for treating hyperlipidemia according to claim 1, wherein $R^1$ and $R^2$ each represents hydrogen, $C_{1-6}$ alkyl, $C_{3-8}$ cycloalkyl or the following formula:

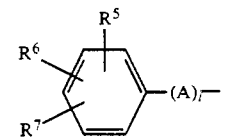

wherein $R^5$, $R^6$ and $R^7$ each represents hydrogen, halogen, $C_{1-6}$ alkyl, $C_{1-6}$ alkoxy, halogen-substituted $C_{1-6}$ alkyl, cyano or nitro; A represents $C_{1-4}$ alkylene; l represents 0 or 1; $R^3$ represents hydrogen; and $R^4$ represents $C_{1-6}$ alkyl.

3. The method for treating hyperlipidemia according to claim 2, wherein $R^1$ and $R^2$ each represents hydrogen, $C_{1-6}$ alkyl or the following formula:

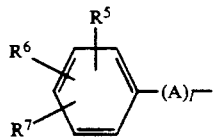

wherein $R^5$, $R^6$ and $R^7$ each represents hydrogen, halogen, $C_{1-6}$ alkyl, halogen-substituted $C_{1-6}$ alkyl, or cyano; A represents $C_{1-4}$ alkylene; l represents 0 or 1; $R^3$ represents hydrogen; and $R^4$ represents $C_{1-6}$ alkyl.

4. The method for treating hyperlipidemia according to claim 3, wherein $R^1$ represents hydrogen.

5. The method for treating hyperlipidemia according to claim 3, wherein $R^1$ represents unsubstituted phenyl-$C_{1-4}$ alkylene or substituted phenyl-$C_{1-4}$ alkylene having halogen atom(s) as the substituent(s) on the phenyl ring.

6. The method for treating hyperlipidemia according to claim 3, wherein $R^1$ represents $C_{1-6}$ alkyl.

7. The method for treating hyperlipidemia according to claim 4, wherein said carboxamide compound is selected from the group consisting of:
4-diethoxyphosphinoylmethyl-N-phenylbenzamide;
4-diethoxyphosphinoylmethyl-N-(4-chlorophenyl)-benzamide;
4-diethoxyphosphinoylmethyl-N-(4-bromophenyl)-benzamide;
4-diethoxyphosphinoylmethyl-N-(4-iodophenyl)-benzamide;
4-diethoxyphosphinoylmethyl-N-(4-fluorophenyl)-benzamide;
4-diethoxyphosphinoylmethyl-N-(4-trifluoromethylphenyl)benzamide;
4-diethoxyphosphinoylmethyl-N-(cyanophenyl)-benzamide;
4-diethoxyphosphinoylmethyl-N-(3,4-dicloro-phenyl)-benzamide; and
4-diethoxyphosphinoylmethyl-N-(4-chloro-3-trifluoromethylphenyl)benzamide.

8. The method for treating hyperlipidemia according to claim 5, wherein said carboxamide compound is selected from the group consisting of:
4-diethoxyphosphinoylmethyl-N-benzyl-N-(4-chlorophenyl)benzamide;
4-diethoxyphosphinoylmethyl-N-(4-chlorobenzyl)-N-(4-chlorophenyl)benzamide;
4-diethoxyphosphinoylmethyl-N-benzyl-N-(4-trifluorophenyl)benzamide;
4-diethoxyphosphinoylmethyl-N-benzyl-N-(3,4-dichlorophenyl)benzamide;
4-diethoxyphosphinoylmethyl-N-benzyl-N-(4-chlorobenzyl-N-(3,4-dichlorophenyl)benzamide; and
4-diethoxyphosphinoylmethyl-N-benzyl-N-(4-chloro-3-methylphenyl)benzamide.

9. The method for treating hyperlipidemia according to claim 6, wherein said carboxamide compound is selected from the group consisting of:
4-diethoxyphosphinoylmethyl-N-methyl-N-phenylbenzamide; and
4-diethoxyphosphinoylmethyl-N-(4-chlorophenyl)-N-methylbenzamide.

10. The method for treating hyperlipidemia according to claim 2, wherein said carboxamide compound is consisting from the group consisting of:
4-diethoxyphosphinoylmethyl-N-(4-methylphenyl)-benzamide;
4-diethoxyphosphinoylmethyl-N-(4-methoxyphenyl)-benzamide;
4-diethoxyphosphinoylmethyl-N-(4-nitrophenyl)-benzamide;
4-diethoxyphosphinoylmethyl-N-(2-phenylethyl)benzamide;
4-diethoxyphosphinoylmethyl-N-(4-chlorophenyl-N'-cyclopentylbenzamide; and
4-diethoxyphosphinoylmethyl-N-benzyl-N-(4-nitrophenyl)benzamide.

11. The method for treating hyperlipidemia according to claim 3, wherein $R^1$ represents hydrogen, $R^2$ represents the following formula:

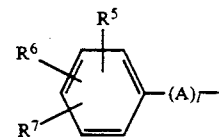

wherein $R^5$, $R^6$ and $R^7$ each represents hydrogen, halogen or cyano, provided that when any one of $R^5$, $R^6$ and $R^7$ represents hydrogen, the remaining two substituents are halogen and cyano, respectively, wherein one of the substituents is bonded at the 4-position of the phenyl ring; $R^3$ represents hydrogen; $R^4$ represents ethyl, and l represents O.

12. The method for treating hyperlipidemia according to claim 11, wherein said carboxamide compound is selected from the group consisting of:
4-diethoxyphosphinoylmethyl-N-(4-bromo-2-cyanophenyl)benzamide;
4-diethoxyphosphinoylmethyl-N-(4-chloro-2-cyanophenyl)benzamide;
4-diethoxyphosphinoylmethyl-N-(4-cyano-2-chlorophenyl)benzamide;
4-diethoxyphosphinoylmethyl-N-(4-iodo-2-cyanophenyl)benzamide;
4-diethoxyphosphinoylmethyl-N-(4-cyano-2-bromophenyl)benzamide; and
4-diethoxyphosphinoylmethyl-N-(4-bromo-3-cyanophenyl)benzamide;
4-diethoxyphosphinoylmethyl-N-(4-cyano-2-iodophenyl)benzamide.

* * * * *